US012564657B2

(12) United States Patent
Sun et al.

(10) Patent No.: US 12,564,657 B2
(45) Date of Patent: Mar. 3, 2026

(54) MOULDABLE ARTIFICIAL BONE COMPOSITE MATERIAL AND PREPARATION METHOD THEREOF

(71) Applicant: SHENZHEN CORLIBER SCIENTIFIC CO., LTD., Shenzhen (CN)

(72) Inventors: Yang Sun, Shenzhen (CN); Dong Xiang, Shenzhen (CN); Xiaoshan Fan, Shenzhen (CN); Jinzhong Zhao, Shanghai (CN); Chaobin He, Singapore (SG); Jia Jiang, Shanghai (CN); Xiaoyu Yan, Shanghai (CN); Liren Wang, Shanghai (CN); Tonghe Zhu, Shanghai (CN)

(73) Assignee: SHENZHEN CORLIBER SCIENTIFIC CO., LTD., Shenzhen (CN)

( * ) Notice: Subject to any disclaimer, the term of this patent is extended or adjusted under 35 U.S.C. 154(b) by 1088 days.

(21) Appl. No.: 17/596,275

(22) PCT Filed: Sep. 6, 2019

(86) PCT No.: PCT/CN2019/104793

§ 371 (c)(1),
(2) Date: Dec. 7, 2021

(87) PCT Pub. No.: WO2021/035795

PCT Pub. Date: Mar. 4, 2021

(65) Prior Publication Data

US 2022/0249735 A1      Aug. 11, 2022

(30) Foreign Application Priority Data

Aug. 31, 2019    (CN) ......................... 201910820127.0

(51) Int. Cl.
A61L 27/12          (2006.01)
A61L 27/18          (2006.01)

(52) U.S. Cl.
CPC ............... *A61L 27/12* (2013.01); *A61L 27/18* (2013.01); *A61L 2430/02* (2013.01)

(58) Field of Classification Search
CPC ...................................................... A61L 24/00
USPC .......................................................... 424/78
See application file for complete search history.

(56) References Cited

U.S. PATENT DOCUMENTS 5,681,873  A      10/1997  Norton et al.

FOREIGN PATENT DOCUMENTS

| CN | 1535668 | A | 10/2004 | |
| CN | 102395388 | A | 3/2012 | |
| CN | 109575249 | A | 4/2019 | |
| CN | 109893677 | A | 6/2019 | |
| WO | WO-9738676 | A1 * | 10/1997 | ............. A61K 9/024 |
| WO | 2000018443 | A1 | 4/2000 | |
| WO | 2003070292 | A1 | 8/2003 | |

* cited by examiner

*Primary Examiner* — Walter E Webb
(74) *Attorney, Agent, or Firm* — AVEK IP, LLC

(57) ABSTRACT

The disclosure provides a mouldable artificial bone composite material and a preparation method thereof. The mouldable artificial bone composite material is characterized in a composition composed of a degradable polymer material and inorganic particles distributed in the polymer material. The average molecular weight of the polymer material is 1,000 Da to 20,000 Da. The inorganic particles are composed of calcium-phosphorus compounds. The artificial bone composite material has a shape of a mouldable plasticine. The disclosure provides an artificial bone composite material that can be freely shaped and injected, and the disclosure further provides a preparation method of the artificial bone composite material.

18 Claims, 2 Drawing Sheets

1

11

12

MOULDABLE ARTIFICIAL BONE COMPOSITE MATERIAL AND PREPARATION METHOD THEREOF

CROSS REFERENCE TO RELATED APPLICATIONS

This application is the United State national stage entry under 37 U.S.C. 371 of PCT/CN2019/104793, filed on Sep. 6, 2019, which claims priority to Chinese application number 201910820127.0, filed on Aug. 31, 2019, the disclosure of which are incorporated by reference herein in their entireties.

FIELD OF THE DISCLOSURE

The present disclosure belongs to the field of biomedical composite materials, and particularly relates to a mouldable artificial bone composite material and a preparation method thereof.

BACKGROUND

The human bone defect is a common disease, Example: trauma, inflammation, bone disease, surgery and other factors can cause bone tissue defect. At present the method of bone defect repair is to repair it with artificial bone materials. Such artificial bone materials usually contain inorganic components such as hydroxyapatite which are the main components of human bones.

Existing Patent Document 1 proposes an injectable artificial bone suspension and a preparation method thereof. The artificial bone injection material is prepared by mixing hydroxyapatite, recombinant human bone morphogenetic protein-2, chitosan solution and heparin saline to form the suspension, The disadvantage of this suspension is that the hydroxyapatite particles are prone to precipitate in the liquid during storage, resulting in uneven dispersion of the hydroxyapatite. In addition, the existing patent document 2 proposes a collagen/light matrix apatite composite material artificial bone, which can be degraded and absorbed in the body.

However, since the artificial bone material of Patent Document 1 needs to rely on water to obtain fluidity, which is easily washed out during injection in a clinical aqueous environment surgery and cannot be used normally, while the material form of Patent Document 2 is a massive hard solid. which cannot be freely plasticized, and that is inconvenient to be used in surgery, and is not easy to fill the bone defect sufficiently and leave a lot of gaps, which will affect bone growth. Therefore, currently a need is required for an artificial bone repair material that can be shaped and injected to meet the filling of different shapes and can be used in minimally invasive surgery in a clinical aqueous environment.

EXISTING TECHNICAL DOCUMENTS

Patent Literature

Patent Document 1: Chinese patent ZL02134874.X
Patent Document 2: Chinese patent ZL201610987810.X

SUMMARY

The following presents a simplified summary of the invention to provide a basic understanding of some aspects of the invention. This summary is not an extensive overview of the invention. It is not intended to identify critical elements or to delineate the scope of the invention. Its sole purpose is to present some concepts of the invention in a simplified form as a prelude to the more detailed description that is presented elsewhere.

The present disclosure is implemented in view of above-described prior arts and aims to provide an artificial bone composite material that can be freely shaped and freely injected and a preparation method thereof.

Therefore, one aspect of the present disclosure provides a mouldable artificial bone composite material, which is a composition obtained by mixing degradable polymer material and inorganic particles distributed in the polymer material, the average molecular weight of the polymer material is 1,000 Da to 20,000 Da, the inorganic particles are composed of calcium-phosphorus compounds, and the artificial bone composite material is in the shape of mouldable plasticine.

In the present disclosure, the degradable polymer material has an average molecular weight of 1,000 Da to 20,000 Da, which can be mixed with inorganic particles and bonded together to form an artificial bone composite material that inorganic particles distributed in the polymer material, The artificial bone composite material is in the shape of mouldable plasticine so that the artificial bone composite material can be freely shaped and injected. In addition, the degradable polymer material is not easy to dissolve in the aqueous environment and can maintain the stable form of the artificial bone composite material in the aqueous environment.

In addition, in the artificial bone composite material according to one aspect of the present disclosure, optionally, the average molecular weight of the polymer material is 4,000 Da to 16,000 Da. Thus, it is possible to balance the mouldability and bone repairability of the artificial bone composite material 1.

In addition, In the artificial bone composite material involved in one aspect of present disclosure, optionally, the polymer material is homopolymer or copolymer of at least one monomer selected from the group consisting of caprolactone and p-dioxanone, or a copolymer formed by caprolactone or p-dioxanone and lactide or glycolide. In this case, a degradable polymer material can be formed, which is beneficial to the application of artificial bone composite materials in the field of orthopedics, especially in the application of absorbable orthopedic materials field.

In addition, In the artificial bone composite material according to one aspect of the present disclosure, optionally, the polymer material is a copolymer of caprolactone and lactide, the molar ratio between caprolactone and lactide is 1:1 to 2.5:1 in the mentioned polymer material, therefore, the polymer material can form the degradable polymer material with desired viscosity and fluidity.

In addition, In the artificial bone composite material according to an aspect of the present disclosure, optionally, the inorganic particles include at least one selected from the group consisting of hydroxyapatite, calcium polyphosphate, and tricalcium phosphate, in this case, since the composition of the inorganic particles is similar to that of human bone tissue, the biological activity and biocompatibility of the artificial bone composite material can be improved.

In addition, in the artificial bone composite material involved in one aspect of the present disclosure, optionally, the mass fraction of the inorganic particles is 10% to 60%, thus, it is possible to improve the repairing effect of the artificial bone composite material while considering the mouldability of the artificial bone composite material.

In addition, in the artificial bone composite material according to one aspect of the present disclosure, optionally, the mass fraction of the inorganic particles is 25% to 50%. Thus, it is possible to further improve the repairing effect of the artificial bone composite material while considering the mouldability of the artificial bone composite material.

In addition, in the artificial bone composite material according to one aspect of the present disclosure, optionally, the artificial bone composite material is in the shape of mouldable plasticine in the first predetermined temperature range, and the artificial bone composite material has fluidity in the second predetermined temperature range, the second predetermined temperature is greater than the first predetermined temperature, in this case, the artificial bone composite material can form with both mouldability and injectability, which is beneficial to the application of the artificial bone composite material in the field of orthopedics.

In addition, in the artificial bone composite material according to one aspect of the present disclosure, optionally, the first predetermined temperature range is 25° C. to 40° C., the second predetermined temperature range is 40° C. to 60° C. In this case, the artificial bone composite material can be conveniently applied in the actual clinical application environment.

In addition, in the artificial bone composite material related to one aspect of the present disclosure, optionally, when a predetermined shear strain is applied to the artificial bone composite material, the storage modulus of the artificial bone composite material is equal to that of the loss modulus. As a result, the artificial bone composite material can have both elasticity and mouldability.

In addition, in the artificial bone composite material according to one aspect of the present disclosure, optionally, when the shear strain applied to the artificial bone composite material is less than the predetermined shear strain, the storage modulus of the artificial bone composite material is greater than that of the loss modulus, when the shear strain applied to the artificial bone composite material is greater than the predetermined shear strain, the loss modulus of the artificial bone composite material is greater than that of the storage modulus. in this case, the artificial bone composite material can exhibit elasticity under small strains, which can withstand a certain force so that the artificial bone composite material can self-shaped and not easy to collapse in the bone defect; meanwhile the artificial bone composite material can exhibit viscous fluidity under large strain. Therefore, the artificial bone composite material cannot only have a certain fluidity, but also have a large deformation value and is irreversible, the artificial bone composite material can be freely shaped and injected In addition, in the artificial bone composite material according to one aspect of the present disclosure, optionally, the predetermined shear strain ranges from 20% to 80%. therefore, the artificial bone composite material can have both elasticity and mouldability in an appropriate shear strain range.

Another aspect of the present disclosure provides a method for preparing a mouldable artificial bone composite material, which including the steps of: preparing a degradable polymer material, and dissolving the polymer material in an organic solvent to obtain a polymer solution; adding inorganic particles composed of calcium-phosphorus compounds into the polymer solution and mixed to obtain a mixture solution; drying the mixture solution in a vacuum to obtain a mixture of the polymer material and the inorganic particles of artificial bone composite material, the polymer material has an average molecular weight of 1,000 Da to 20,000 Da, and in the artificial bone composite material, the inorganic particles are distributed in the polymer material, the artificial bone composite material is in the shape of mouldable plasticine.

In the present disclosure, the polymer material has an average molecular weight of 1,000 Da to 20,000 Da, which have fluidity and viscosity at room temperature, the polymer material and the inorganic particles can be mixed to form an artificial bone composite material in which inorganic particles are distributed in the polymer material. the artificial bone composite material is in the shape of plasticine so that the artificial bone composite material can be freely shaped and used for injection.

In addition, in the artificial bone composite material according to one aspect of the present disclosure, optionally, the average molecular weight of the polymer material is 4,000 Da to 16,000 Da. Therefore, it is possible to prepare an artificial bone composite material 1 that has both mouldability and bone repair properties.

In addition, In the preparation method of the artificial bone composite material related to another aspect of the present disclosure, optionally, when preparing the degradable polymer material, in at least one monomer selected from the group consisting of caprolactone and p-dioxanone, or in two monomers respectively selected from the group consisting of caprolactone and p-dioxanone and the group consisting of lactide and glycolide, adding a catalyst and an initiator, and carry out a thermal reaction to obtain the polymer material, in this case, a degradable polymer material with fluidity and viscosity can be obtained at normal temperature.

In addition, in the preparation method of the artificial bone composite material according to another aspect of the present disclosure, optionally, the catalyst is at least one selected from the group consisting of stannous octoate, zinc oxide, lead stearate, zinc borate, calcium formate and magnesium oxide, the initiator is an alcohol substance, and the thermal reaction that is carried out at temperature of 80° C. to 180° C. in 2 to 48 hours. In this case, the catalyst can catalyze the polymerization during the polymerization reaction of the monomer, the initiator can initiate the polymerization reaction of the monomer, and the thermal reaction can make the polymerization reaction proceed better.

In addition, In the preparation method of the artificial bone composite material according to another aspect of the present disclosure, the mass fraction of the inorganic particles may be 10% to 60%. Therefore, the bone repair ability of the artificial bone composite material can be improved.

According to the present disclosure, it is possible to provide a mouldable artificial bone composite material that can be freely shaped and injected, and a preparation method thereof.

BRIEF DESCRIPTION OF THE DRAWINGS

Illustrative embodiments of the disclosure are described in detail below with reference to the figures.

DETAILED DESCRIPTION

The following describes some non-limiting embodiments of the invention with reference to the accompanying drawings. The described embodiments are merely a part rather than all of the embodiments of the invention. All other embodiments obtained by a person of ordinary skill in the art based on the embodiments of the disclosure shall fall within the scope of the disclosure.

Hereinafter, with reference to the drawings, preferred embodiment method of the present disclosure will be described in detail. In the following description, the same symbols are assigned to the same components, and repeated descriptions are omitted. in addition, the drawings are only schematic diagrams, and the ratio of dimensions between components or the shapes of components may be different from actual ones.

In the present disclosure, unless otherwise specified, "aqueous environment" generally refers to a liquid phase environment containing water.

Figure 1:
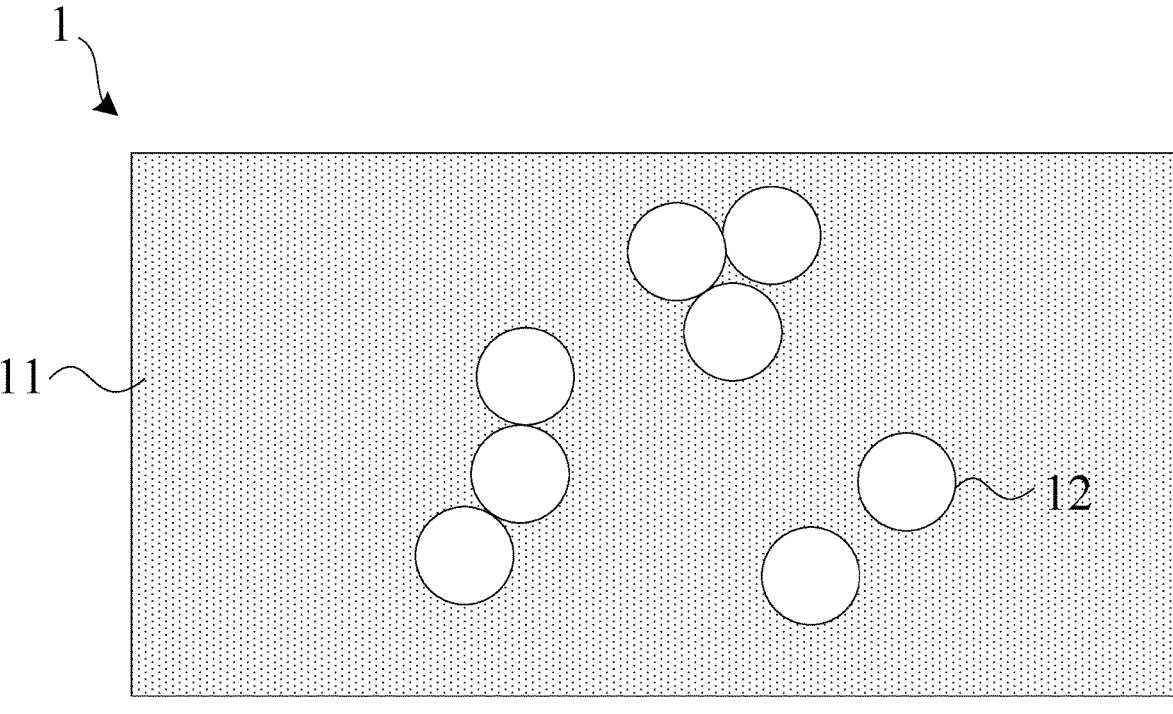
FIG. 1 is a schematic diagram showing the structure of a mouldable artificial bone composite material involved in the example of the present disclosure.

FIG. 1 is a schematic diagram showing the structure of a mouldable artificial bone composite material 1 involved in an example of the present disclosure.

As shown in FIG. 1, in this embodiment method, the mouldable artificial bone composite material 1 may include a degradable polymer material 11 and inorganic particles 12. The average molecular weight of the degradable polymer material 11 may be 1,000 Da to 20,000 Da, and the inorganic particles 12 may be distributed in the polymer material 11, in some examples, the inorganic particles 12 may be composed of calcium-phosphorus compounds, in addition, the artificial bone composite material 1 may be shaped as mouldable plasticine.

In the artificial bone composite material 1 involved in this embodiment, the degradable polymer material 11 has an average molecular weight of 1,000 Da to 20,000 Da, and can be mixed with the inorganic particles 12 to bond the inorganic particles 12 into one and form the inorganic particles 12 distributed in polymer material 11 of artificial bone composite material 1, the artificial bone composite material 1 is shaped as mouldable plasticine, so that which can be freely shaped and can be used by injection, in addition, the degradable polymer material 11 is not easy to dissolve in an aqueous environment, and the artificial bone composite material 1 can maintain a stable form in an aqueous environment.

In some examples, in the first predetermined temperature range, the artificial bone composite material 1 may be shaped as mouldable plasticine, in other words, in the first predetermined temperature range, the artificial bone composite material can be freely shaped, in addition, in some examples, the first predetermined temperature may range from 25° C. to 40° C., in this case, the artificial bone composite material 1 can be conveniently applied in the actual clinical application environment. for example, the first predetermined temperature may be 25° C., 26° C., 27° C., 28° C., 29° C., 30° C., 31° C., 32° C., 33° C., 34° C., 35° C., 36° C., 37° C., 38° C., 39° C. or 40° C.

In addition, in some examples, the artificial bone composite material 1 may have fluidity in the second predetermined temperature range. The second predetermined temperature is greater than the first predetermined temperature, in this case, the artificial bone composite material 1 can have both mouldability and injectability, which is beneficial to the application of the artificial bone composite material 1 in the field of orthopedics, In other words, when the artificial bone composite material 1 is heated to the second predetermined temperature, the artificial bone composite material 1 has fluidity, this will facilitate the implantation operation of the artificial bone composite material 1, so it can be used for injection, for example, which can be injected with the injection tube, in this case, heating can improve the fluidity of the artificial bone composite material 1, thus can facilitate the injection of the artificial bone composite material 1.

In some examples, the second predetermined temperature range may be between 40° C. and 60° C., in this case, the artificial bone composite material 1 can be conveniently applied in the actual clinical application environment. for example, the second predetermined temperature may be 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C.

In some examples, the polymer material 11 may have fluidity and viscosity. in addition, in some examples, the polymer material 11 may have fluidity and viscosity at temperature 20° C. to 60° C.

In some examples, the polymer material 11 may be a degradable polymer material 11, In addition, in some examples, the average molecular weight of the polymer material 11 may be 1,000 Da to 20,000 Da, for example, the average molecular weight of the polymer material 11 may be 1,000 Da, 2,000 Da, 3,000 Da, 4,000 Da, 5,000 Da, 6,000 Da, 7,000 Da, 8,000 Da, 9,000 Da, 10,000 Da, 11,000 Da, 12,000 Da, 13,000 Da, 14,000 Da, 15,000 Da, 16,000 Da, 17,000 Da, 18,000 Da, 19,000 Da, 20,000 Da and the like.

In this embodiment, the average molecular weight of the polymer material 11 is the number average molecular weight of the polymer material 11, in other words, the number average molecular weight of the polymer material 11 may be 1,000 Da to 20,000 Da. In addition, in some examples, the average molecular weight of the polymer material 11 can be measured by a time-of-flight mass spectrometer, a nuclear magnetic resonance instrument, or a gel permeation chromatography method. In addition, in some examples, the number average molecular weight of the polymer material 11 may be measured by a time-of-flight mass spectrometer, a nuclear magnetic resonance instrument, or a gel permeation chromatography method.

In some examples, in gel permeation chromatography, for example, tetrahydrofuran (THF) can be used as a solvent to dissolve the polymer material 11 to form a sample solution to be tested, tetrahydrofuran is used as the mobile phase, and polystyrene is used as the reference standard of the molecular weight, the sample solution is measured in gel permeation chromatography to obtain the average molecular weight (number average molecular weight) of the polymer material 11.

In this embodiment, as described above, the average molecular weight of the polymer material 11 may be 1,000 Da to 20,000 Da. if the average molecular weight of the polymer material 11 is less than 1,000 Da, the polymer material 11 can be difficult to bond the inorganic particles 12, so the inorganic particles 12 in the artificial bone composite material 1 are easy to fall off and cannot be stably formed in water, and the inorganic particles 12 fall off will be easily lead to insufficient osteogenesis. If the average molecular weight of the polymer material 11 is greater than 20,000 Da, the fluidity of the polymer material 11 is poor, So the artificial bone composite material 1 mixed with the inorganic particles 12 will become too hard and be difficult to be shaped freely.

In some examples, for the purpose of considering the mouldability and bone repairability of the artificial bone composite material 1, preferably, the average molecular weight of the polymer material 11 may be 4,000 Da to 16,000 Da.

In this embodiment, as described above, preferably, the average molecular weight of the polymer material 11 may be 4,000 Da to 16,000 Da. In some examples, if the average molecular weight of the polymer material 11 is less than 4,000 Da and less than 1,000 Da, the inorganic particles 12 in the artificial bone composite material 1 are easy to fall off when exposed to water, and are easy to swell in the early stage of bone defect filling and implantation, which is likely to cause negative effect to osteogenesis, In other examples, if the average molecular weight of the polymer material 11 is greater than 16,000 Da, the mould resistance of artificial bone composite material 1 is larger.

In some examples, the polymer material 11 may be a homopolymer or copolymer of at least one monomer selected from the group consisting of caprolactone and p-dioxanone, or may be the copolymer formed by caprolactone to p-dioxanone and lactide or glycolide, In this case, the degradable polymer material 11 can be formed, which is beneficial to the application of the artificial bone composite material 1 in the field of orthopedics, especially the application in the field of absorbable orthopedic materials, for example, the polymer material 11 may be a homopolymer of caprolactone or p-dioxanone, or may be a copolymer of caprolactone and p-dioxanone, a copolymer of caprolactone and lactide or glycolide and a copolymer of p-dioxanone and lactide or glycolide.

In some examples, the polymer material 11 may be a copolymer of caprolactone and lactide, and in the polymer material 11, the molar ratio of caprolactone to lactide is 1:1 to 2.5:1, thereby, the degradable polymer material 11 can form the characteristics with desired viscosity and fluidity. For example, in the polymer material 11, the molar ratio between caprolactone and lactide may be 1:1, 1.2:1, 1.5:1, 1.8:1, 2:1, 2.3:1, or 2.5:1.

In some examples, the mass fraction of the polymer material 11 may be 40% to 90%, in this case, the mouldability of the artificial bone composite material 1 can be improved, For example, the mass fraction of the polymer material 11 may be 40%, 45%, 50%, 55%, 60%, 65%, 70%, 75%, 80%, 85%, 90%, and the like.

In addition, in this embodiment, since the polymer material 11 itself does not contain water, which will not evaporate and not easy to change the properties under normal temperature and pressure, so the shape of the artificial bone composite material 1 can be stably maintained for a long time and will not be dissolved by water in an aqueous environment, so that the artificial bone composite material 1 can keep the stable shape in water.

In some examples, the inorganic particles 12 may include at least one selected from the group consisting of hydroxyapatite, calcium polyphosphate, and tricalcium phosphate, In this case, since the composition of the inorganic particles 12 is similar to human bone tissue, the biological activity and biocompatibility of the artificial bone composite material 1 can be improved.

In addition, in this embodiment, the inorganic particles 12 are not limited to the above-mentioned hydroxyapatite, calcium polyphosphate, tricalcium phosphate and the like, in this embodiment, the inorganic particles 12 may also contain other substances similar to the composition of the human bone tissue, so the repairing effect of the artificial bone composite material 1 on the human bone tissue can also be improved.

In some examples, the mass fraction of the inorganic particles 12 may be 10% to 60%. Therefore, it is possible to improve the repairing effect of the artificial bone composite material on the bone while considering the mouldability of the artificial bone composite material, for example, the mass fraction of the inorganic particles 12 may be 10%, 15%, 20%, 25%, 30%, 35%, 40%, 45%, 50%, 55% or 60%.

In some examples, if the mass fraction of the inorganic particles 12 is less than 10%, after the artificial bone composite material 1 is implanted in the body (the body of a human or animal body), the inorganic particles 12 are not enough to cause the release of the inorganic particles 12 calcium, phosphorus and other elements are insufficient, therefore, which is difficult to effectively help the growth and repair of bones. in other words, if the mass fraction of the inorganic particles 12 is less than 10%, the osteogenic property of the artificial bone composite material 1 is insufficient, and the ability to promote bone repair is poor.

In some examples, if the mass fraction of the inorganic particles 12 is higher than 60%, the amount of the inorganic particles 12 in the polymer material 11 that can be distributed in the polymer structure formed by the polymer material 11 is easily saturated, thus it is difficult to continue to mix with more inorganic particles 12, resulting in the formed artificial bone composite material 1 to easily fall off, that is the artificial bone composite material 1 will fall off excess inorganic particles 12.

In some examples, in order to consider both the mouldability and the bone repair effect of the artificial bone composite material, preferably, the mass fraction of the inorganic particles 12 may be 25% to 50%, therefore, while considering the mouldability of the artificial bone composite material, the repairing effect of the artificial bone composite material on the bone can be further improved.

In addition, in some examples, preferably, the inorganic particles 12 may be rigid particles, in some examples, the inorganic particles 12 may be rigid particles with a Young's modulus greater than $2 \times 10^{11}$ Pa, in this case, the mechanical strength of the artificial bone composite material 1 can be improved.

In addition, in this embodiment, the shape of the inorganic particles 12 is not particularly limited, for example, in some examples, the inorganic particles 12 may be spherical, however, this embodiment is not limited to this, in other examples, the inorganic particles 12 may be ellipsoidal, irregular three-dimensional and the like.

In addition, in this embodiment, the average particle diameter of the inorganic particles 12 is not particularly limited, in some examples, the average particle diameter of the inorganic particles 12 may be 5 nm to 200 μm, for example, the average particle diameter of the inorganic particles 12 may be 5 nm, 10 nm, 30 nm, 50 nm, 100 nm, 200 nm, 500 nm, 1 μm, 2 μm, 5 μm, 10 μm, 20 μm, 30 μm, 50 μm, 80 μm, 100 μm, 130 μm, 150 μm, 180 μm or 200 μm, the average particle size of the above mentioned inorganic particles 12 can be selected according to different usage scenarios.

In some examples, the surface of the inorganic particles 12 may be modified, for example, covering the surface of the inorganic particles 12 with an adhesive layer that is easily combined with the polymer material 11, in this case, the binding strength between the inorganic particles 12 and the polymer material 11 can be increased, so that the inorganic particles 12 can be better bonded into one body, in some examples, the surface of the inorganic particles 12 may be covered with polyethyleneimine.

In addition, in some examples, the artificial bone composite material 1 may include growth factors. In this case, which can better promote the repair and regeneration of bone tissue, in some examples, the growth factor may be at least one selected from the group consisting of collagen, bone morphogenetic protein-2, fibroblast growth factor-2, transforming growth factor-β, insulin-like growth factor-1 and, platelet-derived growth factor.

In addition, in some examples, the artificial bone composite material 1 may also include an antibacterial substance, as a result, which can reduce re-infection of the bone defect site and accelerate healing, In some examples, the antibacterial substance may be antibacterial ions, sulfonamides, quinolones, nitroimidazoles and the like.

In some examples, the antibacterial ion may be at least one selected from the group consisting of silver ion, gallium ion, copper ion, and zinc ion, in addition, the sulfonamides may be one or more selected from the group consisting of trimethoprim, sulfadiazine, sulfamethoxazole, compound sulfamethoxazole, and sulfamethazine, in addition, in some examples, the quinolone may be one or more selected from the group consisting of norfloxacin, ofloxacin, ciprofloxacin, fleroxacin, in addition, the nitroimidazole may be one or more selected from the group consisting of metronidazole, dimetridazole, isopronidazole, secnidazole, ornidazole, tinidazole, and ronidazole.

In some examples, preferably, the artificial bone composite material 1 may be composed of a polymer material 11 and inorganic particles 12, specifically, the artificial bone composite material 1 may be a combination of a degradable polymer material 11 and inorganic particles 12 distributed in the polymer material 11.

In some examples, as described above, the inorganic particles 12 may be distributed in the polymer material 11, in addition, in some examples, in the artificial bone composite material 1, the inorganic particles 12 may be uniformly distributed in the polymer material 11, in other examples, the inorganic particles 12 may also be randomly distributed in the polymer material 11, in addition, in some examples, the inorganic particles 12 may be distributed in the polymer material 11 according to the density of the stepwise arrangement or the regularity of densely arranged in the middle and sparse on both sides.

In this embodiment, the mouldable artificial bone composite material 1 can be freely shaped (for example, doctors can use hands to shape freely), which is convenient for clinical application and can also fill such as the bond defects fully, which can effectively help bone growth and repairing, in addition, since the artificial bone composite material 1 contains the inorganic particles 12 including such as hydroxyapatite, which can make the artificial bone composite material 1 have osteogenesis, which induce the bone growth to complete the repairing, in addition, the artificial bone composite material 1 has degradation gradient layer in the human body, The degradable polymer material 11 can be preferentially and rapidly degraded to form a structure of inorganic particles 12 with a large number of pores, which provides sufficient space for bone growth, The structure of the inorganic particles 12 degradation is slow, which can effectively induce bone tissue to grow in the pores and promote bone repair quickly.

In some examples, the artificial bone composite material 1 may be sterilized. Thereby, the biological safety of the artificial bone composite material 1 can be improved, in addition, in some examples, the artificial bone composite material 1 may be irradiated sterilization. For example, the artificial bone composite material 1 can be sterilized by electron beam, X-ray, or gamma-ray.

In this embodiment, as described above, the artificial bone composite material 1 may have fluidity in the second predetermined temperature range, in this case, the artificial bone composite material 1 is an injectable material, in addition, in some examples, the artificial bone composite material 1 may be heated first before the artificial bone composite material 1 is injected, for example, the artificial bone composite material 1 may be heated to the second predetermined temperature (for example, 40-60° C.), forming a fluidic and viscous mouldable material, and then injected it into an aqueous environment at room temperature.

In some examples, the storage modulus G' and loss modulus G" of the artificial bone composite material 1 are related to the shear strain γ applied to the artificial bone composite material 1, in this embodiment, in some examples, the shear strain γ can range from 0.01% to 100%, for example, the shear strain γ can be 0.01%, 0.1%, 0.5%, 1%, 2%, 5%, 10%, 20%, 40%, 50% s, 80%, 90%, 100%, but the present embodiment is not limited to this, for example, the shear strain γ may be greater than 100%.

In some examples, a rotational rheometer may be used to apply shear strain to the artificial bone material 1, for example, the range of shear strain can be set in the rotational rheometer, applying the vibration amplitude scan to the artificial bone composite material 1 so that the corresponding shear strain γ (for example, 0.01%-100%) can be applied to the artificial bone composite material 1, which can obtain the relationship between the shear strain of the artificial bone composite material 1 and the storage modulus G' and loss modulus G".

In some examples, when the shear strain γ applied to the artificial bone composite material 1 is equal to the predetermined shear strain $γ_0$, the storage modulus G' of the artificial bone composite material 1 is equal to that of the loss modulus G", in other words, when a predetermined shear strain is applied to the artificial bone composite material 1, the storage modulus G' of the artificial bone composite material 1 is equal to the loss modulus G", therefore, the artificial bone composite material 1 can have both elasticity and mouldability, in addition, in some examples, the predetermined shear strain $γ_0$ may range from 20% to 80%, therefore, the artificial bone composite material 1 can be made to have both elasticity and mouldability within a suitable shear strain range.

In some examples, when the shear strain γ applied to the artificial bone composite material 1 is less than the predetermined shear strain $γ_0$, the storage elastic modulus G' of the artificial bone composite material 1 is greater than that of the loss modulus G", under these circumstances, the artificial bone composite material 1 can exhibit elasticity, so that it can withstand a certain force, and the artificial bone composite material 1 can keep the shape in a bone defect without collapsing, in other words, the artificial bone composite material 1 can exhibit elasticity when the artificial bone composite material 1 has a small strain.

In some examples, when the shear strain γ applied to the artificial bone composite material 1 is greater than the predetermined shear strain $γ_0$, the storage modulus G' of the artificial bone composite material 1 is less than that of the loss modulus G", in this case, the artificial bone composite material 1 can exhibit viscous fluidity, therefore, the artificial bone composite material 1 cannot only have certain fluidity, but also have a large deformation value which is irreversible, therefore, the artificial bone composite material 1 can be freely plasticized and injected, in other words, the artificial bone composite material 1 can exhibit viscous fluidity when a large strain is applied, the processes of injection and shaping to the artificial bone composite material are all belong to processes of large strain.

Figure 2:
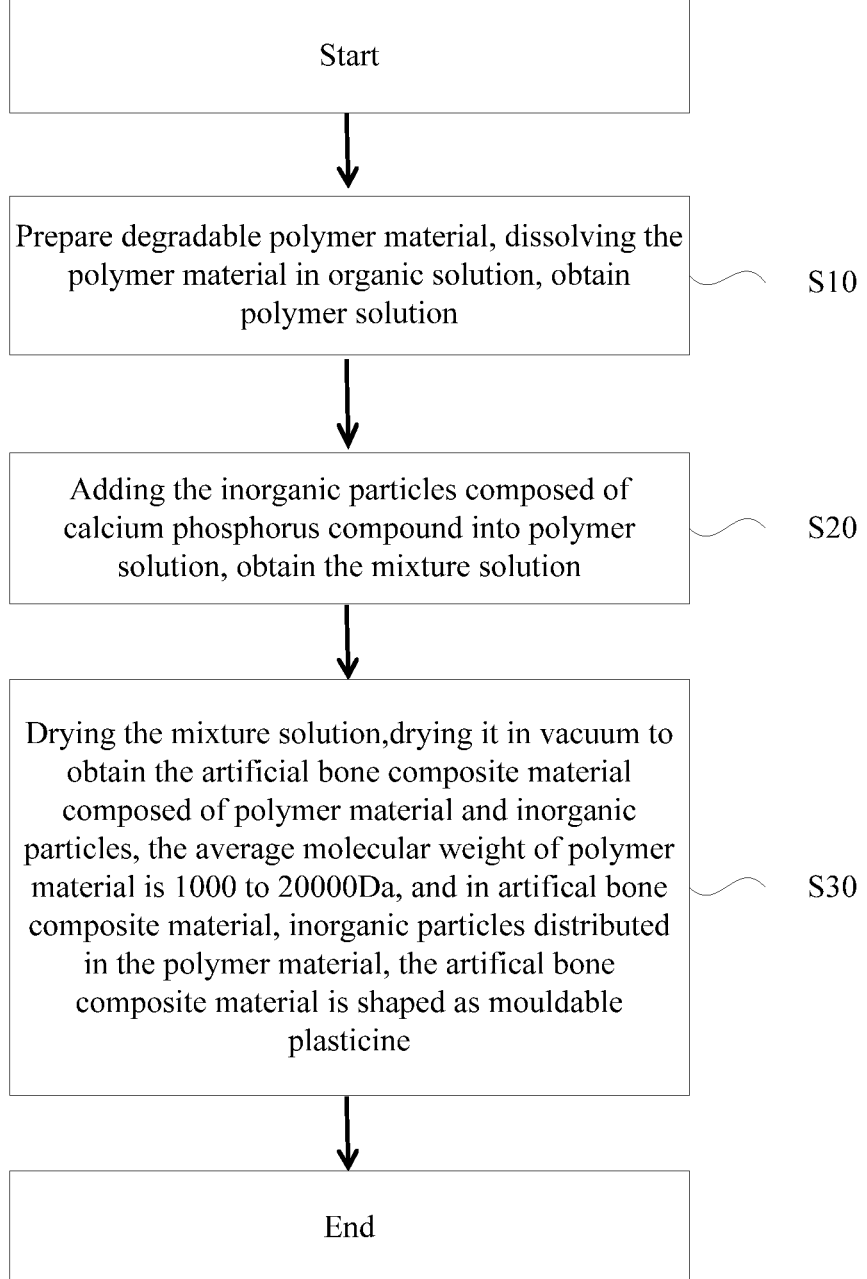
FIG. 2 is a schematic diagram showing the preparation steps of the mouldable artificial bone composite material involved in the example of the present disclosure.

Hereinafter, referring to FIG. 2, the preparation method details of related mouldable artificial bone composite material 1 is described in this disclosure, FIG. 2 is a schematic diagram showing the preparation steps of the mouldable artificial bone composite material 1 involved in the present disclosure.

As shown in FIG. 2, the method for preparing a mouldable artificial bone composite material 1 involved in the present disclosure may include the following steps: preparing a degradable polymer material 11, and dissolving the polymer material 11 in an organic solvent to obtain a polymer solution (step S10); inorganic particles 12 composed of calcium and phosphorus compounds are added to the polymer solution and mixed to obtain a mixture solution (step S20); drying the mixture solution and dry it in a vacuum to obtain the artificial bone composite material 1 composed of polymer material 11 and inorganic particles 12, the average molecular weight of the polymer material 11 is 1,000 Da to 20,000 Da, and in the artificial bone composite material 1, the inorganic particles 12 are distributed in the polymer material 11, and the artificial bone composite material 1 is in the shape of a mouldable plasticine (step S30).

In the preparation method of the mouldable artificial bone composite material 1 involved in this embodiment, the polymer material 11 and the inorganic particles 12 can be mixed to form the artificial bone composite material 1 in which the inorganic particles 12 are distributed in the polymer material 11, the bone composite material 1 is shaped as mouldable plasticine, so that it can be freely shaped and used by injection.

In this embodiment, as described above, in step S10, a degradable polymer material 11 may be prepared, and the polymer material 11 may be dissolved in an organic solvent to obtain a polymer solution.

In step S10, the degradable polymer material 11 may be prepared first. specifically, in preparing the degradable polymer material 11, at least one monomer of caprolactone, p-dioxanone, or 2 monomer selected from the group consisting of caprolactone to p-dioxanone and lactide or glycolide, adding catalyst and initiator to carry out a thermal reaction to obtain the polymer material 11, in this case, a degradable polymer material 11 that has both fluidity and viscosity at room temperature can be obtained.

In some examples, the polymer material 11 with an average molecular weight of 1,000 Da to 20,000 Da can be obtained by controlling the thermal reaction temperature, the thermal reaction time length, the molar ratio between the monomers, the ratio of the monomers to the initiator and the like. The average molecular weight of the polymer material 11 can be measured by a time-of-flight mass spectrometer, a nuclear magnetic resonance instrument, or a gel permeation chromatography method, in addition, the average molecular weight of the polymer material 11 may be the number average molecular weight of the polymer material 11.

In some examples, for the purpose of preparing an artificial bone composite material 1 with both mouldability and bone repair properties, preferably, a polymer material 11 with average molecular weight of 4,000 Da to 16,000 Da can be obtained by controlling the thermal reaction temperature, the thermal reaction time, the molar ratio between the monomers, and the ratio of monomer to the initiator, and the like, that is to say, the artificial bone composite material 1 with the polymer material 11 having average molecular weight of 4,000 Da to 16,000 Da has better performance in free shaping and free injection, and has good bone repair capabilities.

In some examples, the catalyst used in step S10 may be at least one selected from the group consisting of stannous octoate, zinc oxide, lead stearate, zinc borate, calcium formate and magnesium oxide. In this case, the catalyst can catalyze the polymerization during the polymerization reaction of the monomer, in other examples, the catalyst may also be dibutyl tin dilaurate, triethanolamine and the like, in some examples, the initiator may be an alcohol substance, in this case, the initiator can initiate the polymerization reaction of the monomer, for example, the initiator may be at least one of methanol, ethanol, n-propanol, isopropanol, n-butanol, tert-butanol, n-dodecanediol, benzyl alcohol, phenethyl alcohol, phenylpropanol and ethylenedi alcohol.

In some examples, the thermal reaction may be a reaction carried out at a temperature of 80° C. to 180° C. for 2 to 48 hours, in this case, the polymerization reaction can be made to proceed better. in some examples, for example, the thermal reaction may be a reaction that is heated to 80° C. for 48 hours, in other examples, the thermal reaction may be a reaction that is heated to 130° C. for 24 hours, in addition, in some examples, the thermal reaction may be a reaction that is heated to 180° C. for 2 hours, in some examples, The heating temperature of the thermal reaction may also be 90° C., 100° C., 110° C., 120° C., 140° C., 150° C., 160° C., or 170° C., in addition, in some examples, the thermal reaction time may also be 4, 6, 8, 10, 12, 14, 16, 18, 20, or 22 hours.

Next, in step S10, the prepared polymer material 11 may be dissolved in an organic solvent to obtain a polymer solution, in addition, in some examples, the organic solvent may be dichloromethane, trichloromethane, tetrahydrofuran and the like.

In this embodiment, as described above, in step S20, inorganic particles 12 including a calcium-phosphorus compound are added to the polymer solution and mixed to obtain a mixture solution.

In some examples, the inorganic particles 12 including calcium-phosphorus compounds may be prepared first. in some examples, the inorganic particles 12 may be selected one or more from the group consisting of hydroxyapatite, calcium polyphosphate and tricalcium phosphate, in this case, since the composition of the inorganic particles 12 is similar to that of human bone tissue, the biological activity and biocompatibility of the artificial bone composite material 1 can be improved, for example, a blend of calcium hydroxyphosphate and tricalcium phosphate can be prepared as the inorganic particles 12.

In addition, the inorganic particles 12 are not limited to the above-mentioned hydroxyapatite, calcium polyphosphate, tricalcium phosphate and the like, in this embodiment, the inorganic particles 12 may contain other substances similar in composition to the human bone tissue, which can also improve the repairing effect of the artificial bone composite material 1 on the human bone tissue.

In some examples, the surface of the prepared inorganic particles 12 may be modified, therefore, when the inorganic particles 12 and the polymer material 11 are subsequently mixed, the binding force between the inorganic particles 12 and the polymer material 11 can be increased, so the inorganic particles 12 and the polymer material 11 can be better bonded and integrated.

In this embodiment, in step S20, the polymer solution in step S10 and the inorganic particles 12 can be adequately mixed to obtain a mixture solution, in addition, in some examples, the polymer solution and the inorganic particles 12 can be adequately mixed by manual stirring, ultrasonic stirring, magnetic stirring and the like.

In some examples, in step S20, the inorganic particles 12 may be added at a mass ratio of polymer material 11 to that of inorganic particles 12 from 2:3 to 9:1, in other words, in the artificial bone composite material 1, the mass fraction of the inorganic particles 12 may be 10% to 60%, in this case, the mechanical strength of the artificial bone composite material 1 can be improved, and the plasticine shape characteristics of the artificial bone composite material 1 can be ensured, in addition, in order to take into account both the mouldability of the artificial bone composite material and the bone repair effect, preferably, the mass fraction of the inorganic particles 12 may be 25% to 50%.

In some examples, in step S20, the growth factors may be added to the polymer solution, in addition, in some examples, the growth factor may be at least one selected from the group consisting of collagen, bone morphogenetic protein-2, fibroblast growth factor-2, transforming growth factor-0, insulin-like growth factor-1, platelet-derived growth factor.

In some examples, in step S20, the antibacterial substance may be in the polymer solution. In addition, in some examples, the antibacterial substance may be antibacterial ions, sulfonamides, quinolones, nitroimidazoles and the like.

In this embodiment, as described above, in step S30, The mixture solution in step S20 can be dried and dried in a vacuum to obtain the artificial bone composite material 1, in addition, in some examples, the mixture solution can be dried in an oven first, and then dried in a vacuum drying oven.

In some examples, in step S30, the artificial bone composite material 1 may also be sterilized, thereby, the biological safety of the artificial bone composite material 1 can be improved, In addition, In some examples, in step S30, the artificial bone composite material 1 may be irradiated sterilized, for example, the artificial bone composite material 1 can be sterilized by electron beam, X-ray, or gamma-ray.

In order to further illustrate present disclosure, the mouldable artificial bone composite material 1 and the preparation method provided by the present disclosure will be described in detail below in conjunction with examples, and the beneficial effects achieved by the present disclosure will be fully illustrated in conjunction with comparative examples.

[EXAMPLE 1] TO [EXAMPLE 22]

Firstly, the monomers of each of Examples 1 to 22 are prepared first. According to table 1, preparing the monomers of each of Examples 1 to 22, obtaining the monomers having the average molecular weight and type shown in Table 1. Then, the catalysts and initiators shown in Table 1 were added to the monomers of each respective examples of Example 1 to Example 22 to obtain a monomer-containing mixture, according to the reaction temperature and reaction time shown in Table 1, the mixture was heated to a predetermined reaction temperature and reacted for the predetermined time to obtain the degradable polymer materials of each of examples 1 to example 22.

Secondly, take the degradable polymer material of each example (example 1 to example 22), and prepare the sample solution of each example (example 1 to example 22) at the ratio of 0.2 g of polymer material to 1 ml of tetrahydrofuran. Then, using tetrahydrofuran as the mobile phase, and use polystyrene as the molecular weight reference standard, carry out GPC test to obtain the number average molecular weight of the degradable polymer materials of each example (example 1 to example 22).

Then, in each of the examples (example 1 to example 22), the obtained degradable polymer materials were dissolved in dichloromethane as an organic solvent, and the inorganic material was added in a predetermined mass ratio as shown in Table 1, the particles were stirred ultrasonically to obtain the mixture solutions of example 1 to example 22. Finally, the mixture solution was heated and dried and then in vacuum heated and dried to obtain the artificial bone composite material of each example (example 1 to example 22).

The performance test of the artificial bone composite material of each example (example 1 to example 22) prepared according to Table 1 is performed, and the specific process of the performance test is shown as follows:

(1) Rheology test: The artificial bone composite material of each example was placed on a rotary rheometer (model: Anton Paar MCR302) for amplitude scanning, and the scanning condition was shear strain ($\gamma$) 0.01-100%, normal force 0 N, angular frequency 1 rad/s, temperature 37° C., scan to obtain the shear strain $\gamma(x)$-modulus (y, including storage modulus G' and loss modulus G") curve, and then judge the relationship between G' and G" of the artificial bone composite materials of the examples (example 1 to example 22) when the shear strain $\gamma$ is 0.01%-1% and 90%-100%.

(2) Water resistance test: take the artificial bone composite material of each example respectively to make a cube of 10×10×10 mm, weigh the weight of each cube, and then soak it in normal saline at 37° C. to observe the physiological condition of each cube, whether it can be formed stably in salt water, after 24 hours, take it out and dry and then weigh the mass of each cube, calculate the mass ratio of each cube after soaking to before soaking, and according to the mass ratio, judge the status of the inorganic particles of the artificial bone composite material falling off in an aqueous environment in each sample (example 1 to example 22), The result of water resistance test are shown in Table 3.

(3) Shaping test: take 4 g of the artificial bone composite material of each example as test sample, and then knead each test sample by hand at 25° C. to 40° C. to judge whether it can be shaped freely or whether it has fallen powder or not;

(4) Bone defect repair experiment: take the injected artificial bone composite material of each example, heat it to 40° C. to 60° C., and then inject it into the rabbit femoral condyle defect (10 mm depth, 6 mm diameter), and observe the repair effect three months later, the results of bone defect repair are shown in Table 3.

[COMPARATIVE EXAMPLE 1] TO [COMPARATIVE EXAMPLE 12]

Firstly, preparing the monomers of comparative example 1 to comparative example 12 at first, according to Table 1, prepare the monomers of comparative example 1 to comparative example 12, and obtain monomers having the average molecular weight and type shown in Table 1. Then, add catalysts and initiators shown in Table 1 to the monomers of the respective comparative example 1 to comparative example 12 to obtain a monomer-containing mixture, according to the reaction temperature and reaction time shown in Table 1, the mixture was heated to a predetermined reaction temperature and reacted for a predetermined time to obtain the degradable polymer material of each comparative example 1 to comparative example 12.

Secondly, take the degradable polymer materials of each comparative example (comparative example 1 to comparative example 12), and prepare sample solutions of each comparative example (comparative example 1 to comparative example 12) at the ratio of 0.2 g polymer material to 1 ml of tetrahydrofuran, and then use tetrahydrofuran as the mobile phase and polystyrene as the molecular weight reference standard, and use the chromatographic column to carry out GPC test, the number average molecular weight of the degradable polymer materials of each comparative example (comparative example 1 to comparative example 12) can be obtained.

Then, in each comparative example (comparative example 1 to comparative example 12), the obtained degradable polymer materials were dissolved in dichloromethane as an organic solvent, and a predetermined mass ratio of inorganic materials was added as shown in Table 1, the particles were stirred ultrasonically to obtain a mixture solution of comparative example 1 to comparative example 12, finally, the mixture solution was heated and dried and then vacuum heated and dried so that the artificial bone composite material of each comparative example (comparative example 1 to comparative example 12) can be obtained.

The performance test of the artificial bone composite materials of each comparative example (comparative example 1 to comparative example 12) prepared according to Table 1 were performed, and the specific process of the performance test is as follows:

(1) Rheology test: place the artificial bones of each comparative example (comparative example 1 to comparative example 12) on a rotary rheometer (model: Anton Paar MCR302) to perform amplitude scanning, and the scanning condition is shear strain ($\gamma$) 0.01-100%, normal force 0 N, angular frequency 1 rad/s, temperature 37° C., scan to obtain the curve of shear strain $\gamma$(x)-modulus (y, including storage modulus G' and loss modulus G"), and then judge the relationship between G' and G" when the shear strain $\gamma$ of artificial bone composite material of each comparative example (comparative example 1 to comparative example 12) is 0.01%-1% and 90%-100% and 0.01%-100%.

(2) Water resistance test: take the artificial bone composite materials of each comparative example to make 10×10×10 mm cubes, weigh the mass of each cube, and then soak it in normal saline at 37° C. to observe the physiological condition of each cube. whether it can be formed stably in salt water, take it out and dry and then weigh the mass of each cube after 24 hours, calculate the mass ratio of each cube after soaking to before soaking, and according to the mass ratio, judge the status of the inorganic particles of the artificial bone composite material falling off in an aqueous environment in each comparative example. The water resistance test results are shown in Table 3.

(3) Shaping test: take 4 g of the artificial bone composite material of each comparative example as the test sample, and then knead each test sample by hand at 25° C. to 40° C. to judge whether it can be shaped freely and whether it has fallen powder.

(4) Bone defect repair experiment: take the injected artificial bone composite material of each comparative example, heat it to 40° C. to 60° C., and then inject it into the rabbit femoral condyle defect (10 mm depth, 6 mm diameter), and observe the repair effect 3 months later. The results of bone defect repair are shown in Table 3.

TABLE 1

| | Polymer material (Monomer and number average molecular weight) | Catalyst | Initiator | Reaction temperature | Reaction time | Inorganic particle type and mass ratio |
|---|---|---|---|---|---|---|
| Example 1 | Caprolactone, 1,000 Da | Stannous octoate | Dodecanol | 80° C. | 48 h | Hydroxyapatite, 60% |
| Example 2 | Caprolactone and p-dioxanone in a molar ratio of 1:1, 20,000 Da | Stannous octoate | Dodecanol | 80° C. | 48 h | Hydroxyapatite/ Tricalcium Phosphate (mass ratio of 7:3) , 60% |
| Example 3 | Caprolactone, 1,000 Da | Stannous octoate | Ethylene glycol | 120° C. | 36 h | Tricalcium Phosphate, 10% |
| Example 4 | Caprolactone and p-dioxanone in a molar ratio of 1:1, 20,000 Da | Stannous octoate | Ethylene glycol | 120° C. | 36 h | Tricalcium Phosphate, 10% |
| Example 5 | Caprolactone, 1,000 Da | Zinc oxide | Ethanol | 180° C. | 2 h | Hydroxyapatite, 40% |
| Example 6 | Caprolactone and p-dioxanone in a molar ratio of 1:1, 20,000 Da | Zinc oxide | Ethanol | 180° C. | 2 h | Hydroxyapatite, 40% |
| Example 7 | Caprolactone, 4,000 Da | Stannous octoate | Ethylene glycol | 120° C. | 36 h | Hydroxyapatite, 60% |
| Example 8 | Caprolactone, 4,000 Da | Stannous octoate | Ethylene glycol | 120° C. | 36 h | Hydroxyapatite, 40% |
| Example 9 | Caprolactone, 4,000 Da | Stannous octoate | Ethylene glycol | 120° C. | 36 h | Hydroxyapatite, 10% |
| Example 10 | Caprolactone and p-dioxanone in a molar ratio of 1:1, 10,000 Da | Magnesium Oxide | Methanol | 130° C. | 24 h | Hydroxyapatite, 60% |
| Example 11 | Caprolactone and p-dioxanone in a molar ratio of 1:1, 10,000 Da | Magnesium Oxide | Methanol | 130° C. | 24 h | Tricalcium Phosphate, 10% |
| Example 12 | Caprolactone and p-dioxanone in a molar ratio of 1:1, 10,000 Da | Stannous octoate | Dodecanol | 80° C. | 48 h | Tricalcium Phosphate, 40% |
| Example 13 | Caprolactone and p-dioxanone in a molar ratio of 1:1, 16,000 Da | Magnesium Oxide | Ethanol | 130° C. | 24 h | Hydroxyapatite, 60% |
| Example 14 | Caprolactone and p-dioxanone in a molar ratio of 1:1, 16,000 Da | Magnesium Oxide | Ethanol | 130° C. | 24 h | Hydroxyapatite, 40% |

TABLE 1-continued

| | Polymer material (Monomer and number average molecular weight) | Catalyst | Initiator | Reaction temperature | Reaction time | Inorganic particle type and mass ratio |
|---|---|---|---|---|---|---|
| Example 15 | Caprolactone and p-dioxanone in a molar ratio of 1:1, 16,000 Da | Stannous octoate | Dodecanol | 80° C. | 48 h | Hydroxyapatite, 10% |
| Example 16 | Caprolactone and p-dioxanone in a molar ratio of 1:1, 10,000 Da | Stannous octoate | Dodecanol | 80° C. | 48 h | Hydroxyapatite/ Tricalcium Phosphate (mass ratio of 7:3), 40% |
| Example 17 | Caprolactone and p-dioxanone in a molar ratio of 1:1, 10,000 Da | Stannous octoate | Ethylene glycol | 120° C. | 36 h | Hydroxyapatite, 40% |
| Example 18 | Caprolactone, 10,000 Da | Stannous octoate | Ethylene glycol | 120° C. | 36 h | Hydroxyapatite, 40% |
| Example 19 | Caprolactone and lactide in a molar ratio of 2.5:1, 10,000 Da | Stannous octoate | Ethylene glycol | 120° C. | 36 h | Hydroxyapatite, 40% |
| Example 20 | Caprolactone and lactide in a molar ratio of 2:1, 10,000 Da | Stannous octoate | Ethylene glycol | 120° C. | 36 h | Hydroxyapatite, 40% |
| Example 21 | Caprolactone and lactide in a molar ratio of 1.5:1, 10,000 Da | Stannous octoate | Ethylene glycol | 120° C. | 36 h | Hydroxyapatite, 40% |
| Example 22 | Caprolactone and lactide in a molar ratio of 1:1, 10,000 Da | Stannous octoate | Ethylene glycol | 120° C. | 36 h | Hydroxyapatite, 40% |

TABLE 2

| | Polymer material (monomer type and number average molecular weight) | Catalyst | Initiator | Reaction temperature | Reaction time | Inorganic particles type and mass ratio |
|---|---|---|---|---|---|---|
| Comparative example 1 | Caprolactone, 900 Da | Stannous octoate | Dodecanol | 80° C. | 48 h | Hydroxyapatite, 60% |
| Comparative example 2 | Caprolactone and p-dioxanone in a molar ratio of 1:1, 20,736Da | Stannous octoate | Dodecanol | 80° C. | 48 h | Hydroxyapatite/ Tricalcium Phosphate(mass ratio of 7:3), 60% |
| Comparative example 3 | Caprolactone, 900 Da | Stannous octoate | Dodecanol | 80° C. | 48 h | Tricalcium Phosphate, 10% |
| Comparative example 4 | Caprolactone and p-dioxanone in a molar ratio of 1:1, 20,736Da | Stannous octoate | Dodecanol | 80° C. | 48 h | Tricalcium Phosphate, 10% |
| Comparative example 5 | Caprolactone, 1,000 Da | Stannous octoate | Dodecanol | 80° C. | 48 h | Hydroxyapatite, 65% |
| Comparative example 6 | Caprolactone, 1,000 Da | Stannous octoate | Dodecanol | 80° C. | 48 h | Tricalcium Phosphate, 8% |
| Comparative example 7 | Caprolactone and p-dioxanone in a molar ratio of 1:1, 20,000 Da | Stannous octoate | Dodecanol | 80° C. | 48 h | Hydroxyapatite/ Tricalcium Phosphate(mass ratio of 7:3), 65% |
| Comparative example 8 | Caprolactone and p-dioxanone in a molar ratio of 1:1, 20,000 Da | Stannous octoate | Dodecanol | 80° C. | 48 h | Tricalcium Phosphate, 8% |
| Comparative example 9 | Caprolactone, 900 Da | Stannous octoate | Dodecanol | 80° C. | 48 h | Hydroxyapatite, 65% |
| Comparative example 10 | Caprolactone, 900 Da | Stannous octoate | Dodecanol | 80° C. | 48 h | Tricalcium Phosphate, 8% |
| Comparative example 11 | Caprolactone and p-dioxanone in a molar ratio of 1:1, 20,736Da | Stannous octoate | Dodecanol | 80° C. | 48 h | Hydroxyapatite, 65% |
| Comparative example 12 | Caprolactone and p-dioxanone in a molar ratio of 1:1, 20,736Da | Stannous octoate | Dodecanol | 80° C. | 48 h | Tricalcium Phosphate, 8% |

TABLE 3

| | Relationship between G' and G" | Water resistance experiment result | Performance description |
|---|---|---|---|
| Example 1 | G' > G" when γ is 0.01%-1%, G" > G' when γ is 90%-100% | 78% | Can be shaped freely; stable molding; Easy to drop powder when exposed to water; Rabbit bone defect is easy to swell in the early stage of implantation, But the repair effect is ideal in 3 months |
| Example 2 | G' > G" when γ is 0.01%-1%, G" > G' when γ is 90%-100% | 96% | Very hard, high resistance to be shaped; Stable molding; no powder fall off; Rabbit bone defect repair effect is ideal in 3 months |
| Example 3 | G' > G" when γ is 0.01%-1%, G" > G' when γ is 90%-100% | 90% | Can be shaped freely; stable molding; Rabbit bone defect is easy to swell in the early stage of implantation, But the repair effect is ideal in 3 months |
| Example 4 | G' > G" when γ is 0.01%-1%, G" > G' when γ is 90%-100% | 95% | Very hard, high resistance to be shaped; Stable molding; no powder fall off; Rabbit bone defect repair effect is ideal in 3 months |
| Example 5 | G' > G" when γ is 0.01%-1%, G" > G' when γ is 90%-100% | 80% | Can be shaped freely; stable molding; Easy to drop powder when exposed to water; Rabbit bone defect is easy to swell in the early stage of implantation, But the repair effect is ideal in 3 months |
| Example 6 | G' > G" when γ is 0.01%-1%, G" > G' when γ is 90%-100% | 98% | Very hard, high resistance to be shaped; Stable molding; no powder fall off; Rabbit bone defect repair effect is ideal in 3 months |
| Example 7 | G' > G" when γ is 0.01%-1%, G" > G' when γ is 90%-100% | 95% | Can be shaped freely; stable molding; no powder fall off; Rabbit bone defect repair effect is ideal in 3 months |
| Example 8 | G' > G" when γ is 0.01%-1%, G" > G' when γ is 90%-100%' | 93% | Can be shaped freely; stable molding; no powder fall off; Rabbit bone defect repair effect is ideal in 3 months |
| Example 9 | G' > G" when γ is 0.01%-1%, G" > G' when γ is 90%-100% | 96% | Can be shaped freely; stable molding; no powder fall off; Rabbit bone defect repair effect is ideal in 3 months |
| Example 10 | G' > G" when γ is 0.01%-1%, G" > G' when γ is 90%-100% | 99% | Can be shaped freely; stable molding; no powder fall off; Rabbit bone defect repair effect is ideal in 3 months |
| Example 11 | G' > G" when γ is 0.01%-1%, G" > G" when γ is 90%-100% | 100% | Can be shaped freely; stable molding; no powder fall off; Rabbit bone defect repair effect is ideal in 3 months |
| Example 12 | G' > G" when γ is 0.01%-1%, G" > G' when γ is 90%-100% | 96% | Can be shaped freely; stable molding; no powder fall off; Rabbit bone defect repair effect is ideal in 3 months |
| Example 13 | G' > G" when γ is 0.01%-1%, G" > G' when γ is 90%-100% | 95% | Can be shaped freely; stable molding; no powder fall off; Rabbit bone defect repair effect is ideal in 3 months |
| Example 14 | G' > G" when γ is 0.01%-1%, G" > G' when γ is 90%-100% | 99% | Can be shaped freely; stable molding; no powder fall off; Rabbit bone defect repair effect is ideal in 3 months |
| Example 15 | G' > G" when γ is0.01%-1%, G" > G' when γ is 90%-100% | 92% | Can be shaped freely; stable molding; no powder fall off; Rabbit bone defect repair effect is ideal in 3 months |
| Example 16 | G' > G" when γ is 0.01%-1%, G" > G' when γ is 90%-100% | 97% | Can be shaped freely; stable molding; no powder fall off; Rabbit bone defect repair effect is ideal in 3 months |
| Example 17 | G' > G" when γ is 0.01%-1%, G" > G' when γ is 90%-100% | 92% | Can be shaped freely; stable molding; no powder fall off; Rabbit bone defect repair effect is ideal in 3 months |
| Example 18 | G' > G" when γ is 0.01%-1%, G" > G' when γ is 90%-100% | 93% | Can be shaped freely; stable molding; no powder fall off; Rabbit bone defect repair effect is ideal in 3 months |

TABLE 3-continued

| | Relationship between G' and G" | Water resistance experiment result | Performance description |
|---|---|---|---|
| Example 19 | G' > G" when γ is 0.01%-1%, G" > G' when γ is 90%-100% | 94% | Can be shaped freely; stable molding; no powder fall off; Rabbit bone defect repair effect is ideal in 3 months |
| Example 20 | G' > G" when γ is 0.01%-1%, G" > G' when γ is 90%-100% | 96% | Can be shaped freely; stable molding; no powder fall off; Rabbit bone defect repair effect is ideal in 3 months |
| Example 21 | G' > G" when γ is 0.01%-1%, G" > G' when γ is 90%-100% | 97% | Can be shaped freely; stable molding; no powder fall off; Rabbit bone defect repair effect is ideal in 3 months |
| Example 22 | G' > G" when γ is 0.01%-1%, G" > G' when γ is 90%-100% | 95% | Can be shaped freely; stable molding; no powder fall off; Rabbit bone defect repair effect is ideal in 3 months |
| Comparative example 1 | G" > G' when γ is 0.01%-100% | 50% | Cannot be shaped freely; Powder fall off; Rabbit bone defect repair cannot be completed |
| Comparative example 2 | G' > G" when γ is 0.01%-100% | 92% | Cannot be shaped freely, very hard |
| Comparative example 3 | G" > G' when γ is 0.01%-100% | 65% | Powder is easy to fall of |
| Comparative example 4 | G' > G" when γ is 0.01%-100% | 96% | Cannot be shaped freely, very hard |
| Comparative example 5 | G' > G" when γ is 0.01%-100% | 75% | Cannot be shaped stably; Powder fall off; Rabbit bone defect repair cannot be completed |
| Comparative example 6 | G" > G' when γ is 0.01%-100% | 90% | Rabbit bone defect repair effect is not well in 3 months |
| Comparative example 7 | G' > G" when γ is 0.01%-100% | 85% | Hard; cannot be shaped freely; Powder fall off; Rabbit bone defect repair cannot be completed |
| Comparative example 8 | G' > G" when γ is 0.01%-1%, G" > G' when γ is 90%-100% | 96% | Rabbit bone defect repair effect is not well in 3 months |
| Comparative example 9 | G' > G" when γ is 0.01%-1%, G" > G' when γ is 90%-100% | 40% | Cannot be shaped stably; Powder fall off; Rabbit bone defect repair cannot be completed |
| Comparative example 10 | G" > G' when γ is 0.01%-100% | 75% | Powder is easy to fall off; Rabbit bone defect repair effect is not well in 3 months |
| Comparative example 11 | G' > G" when γ is 0.01%-100% | 85% | Very hard; cannot be shaped freely; powder fall off; Rabbit bone defect repair cannot be completed |
| Comparative example 12 | G' > G" when γ is 0.01%-100% | 95% | Rabbit bone defect repair cannot be completed |

It can be seen from Table 3 that compared with the comparative examples; the artificial bone composite materials obtained in the examples (example 1 to example 22) G" is greater than G' when the shear strain γ is 90%-100%. That is, the artificial bone composite material exhibits viscous fluidity at large strain, and the artificial bone composite material can be kneaded and shaped freely by hand, and the inorganic particle powder is not easy to fall off (no powder fall off). Among them, although the artificial bone composite materials of example 2, example 4 and example 6 are very hard, the artificial bone composite materials in example 2, example 4 and example 6 can still be shaped by hand, but the shaping resistance will be large.

In addition, the artificial bone composite materials obtained in most of the examples (examples except example 1, example 3 and example 5) can be formed stably in an aqueous environment, and the water resistance test results are all above 90%, that is the water resistance performance is excellent, and also the artificial bone composite material has little loss of inorganic particles falling off in the aqueous environment, in addition, the artificial bone composite material obtained in each example has an ideal repairing effect in the rabbit bone defect filling and repairing experiment within three months. Moreover, although the water resistance test results of the artificial bone composite materials in example 1, example 3 and example 5 are below 90%, which is the artificial bone composite materials in example 1, example 3 and example 5 powder are easy to fall off when exposed to water, making rabbit bone defect filling and implantation easy to swell in the early stage, however, the artificial bone composite material obtained in example 1, example 3 and example 5 still have ideal repairing effect in rabbit bone defect filling and repairing experiments in three months.

In summary, the artificial bone composite material obtained in example 1 to example 22 having the polymer material with an average molecular weight of 1,000 Da to 20,000 Da can be freely shaped and injected, and it has good bone repair capabilities. In addition, the artificial bone composite material having the polymer material which have a preferred average molecular weight of 4,000 Da to 16,000 Da, has better free shaping and free injection performance, and it also has a good bone repair ability.

In comparison, the artificial bone composite material obtained in comparative example 1 to comparative example 12 cannot simultaneously achieve all the performance effects as the examples implemented as above embodiment.

Although the above combined with the attached drawings and the embodiment methods give a specific explanation of this disclosure, which can be in understandable way, the above description does not restrict this disclosure in any form, the technical person in this field may make modification and change to this disclosure as the need without deviating from the essence and scope of this disclosure, these modification and change are all in the scope of this disclosure.

Many different arrangements of the various components depicted, as well as components not shown, are possible without departing from the spirit and scope of the disclosure. Embodiments of the disclosure have been described with the intent to be illustrative rather than restrictive. Alternative embodiments will become apparent to those skilled in the art that do not depart from its scope. A skilled artisan may develop alternative means of implementing the aforementioned improvements without departing from the scope of the disclosure.

It will be understood that certain features and subcombinations are of utility and may be employed without reference to other features and subcombinations and are contemplated within the scope of the claims. Unless indicated otherwise, not all steps listed in the various figures need be carried out in the specific order described.

What is claimed is:

1. A mouldable artificial bone composite material, wherein:

the mouldable artificial bone composite material is a composition obtained by mixing a degradable polymer material and inorganic particles distributed in said polymer material;

an average molecular weight of the polymer material is 4,000 Da to 16,000 Da;

the polymer material is a copolymer formed by caprolactone or p-dioxanone and lactide or glycolide;

the inorganic particles are composed of calcium-phosphorus compounds;

in a first predetermined temperature range, the artificial bone composite material is in a shape of a mouldable plasticine;

in a second predetermined temperature range, the polymer material has fluidity;

the second predetermined temperature is greater than the first predetermined temperature;

the first predetermined temperature range is 25° C. to 40° C.; and the second predetermined temperature range is 40° C. to 60° C.

2. The artificial bone composite material according to claim 1, wherein the first predetermined temperature range is 25° C. to 36° C.

3. The artificial bone composite material according to claim 1, wherein:

the polymer material is the copolymer formed by caprolactone and lactide; and the molar ratio between caprolactone and lactide is 1:1 to 2.5:1.

4. Artificial bone composite material according to claim 1, wherein the inorganic particles contain at least one item selected from the group consisting of hydroxyapatite, calcium polyphosphate, and tricalcium phosphate.

5. The artificial bone composite material according to claim 1, wherein a mass fraction of the inorganic particles is 10% to 60%.

6. The artificial bone composite material according to claim 5, wherein the mass fraction of the inorganic particles is 25% to 50%.

7. The artificial bone composite material according to claim 1, wherein when a predetermined shear strain is applied to the artificial bone composite material, a storage modulus of the artificial bone composite material is equal to a loss modulus of the artificial bone composite material.

8. The artificial bone composite material according to claim 7, wherein:

when the shear strain applied to the artificial bone composite material is less than the predetermined shear strain, the storage modulus of the artificial bone composite material is greater than the loss modulus of the artificial bone composite material; and when the shear strain applied to the artificial bone composite material is greater than the predetermined shear strain, the loss modulus of the artificial bone composite material is greater than the storage modulus of the artificial bone composite material.

9. The artificial bone composite material according to claim 7, wherein a range of the predetermined shear strain is 20% to 80%.

10. A method for preparing a mouldable artificial bone composite material, comprising the steps of:

adding a catalyst, an initiator, a first monomer, and a second monomer to carry out a thermal reaction to obtain a degradable polymer material, the first monomer being selected from the group consisting of caprolactone and p-dioxanone and the second monomer being selected from the group consisting of lactide or glycolide;

dissolving the polymer material in an organic solvent to obtain a polymer solution;

adding and mixing inorganic particles composed of calcium-phosphorus compounds into the polymer solution to obtain a mixture solution; and drying the mixture solution in a vacuum to obtain the artificial bone composite material composed of the polymer material and the inorganic particles;

wherein:

an average molecular weight of the polymer material is 4,000 Da to 16,000 Da;

the inorganic particles are distributed in the polymer material;

in a first predetermined temperature range, the artificial bone composite material is in a shape of a mouldable plasticine;

in a second predetermined temperature range, the polymer material has fluidity;

the second predetermined temperature is greater than the first predetermined temperature;

the first predetermined temperature range is 25° C. to 40° C.; and the second predetermined temperature range is 40° C. to 60° C.

11. The preparing method according to claim 10, wherein the first predetermined temperature range is 25° C. to 36° C.

12. The preparing method according to claim 10, wherein:

the catalyst comprises at least one item selected from the group consisting of stannous octoate, zinc oxide, lead stearate, zinc borate, calcium formate, and magnesium oxide;

the initiator is an alcohol substance; and the thermal reaction is carried out at a temperature of 80° C. to 180° C. for 2 to 48 hours.

13. The preparing method according to claim 10, wherein the inorganic particles comprising at least one item selected from the group consisting of hydroxyapatite, calcium polyphosphate, tricalcium Phosphate.

14. The preparing method according to claim 10, wherein a mass fraction of the inorganic particles is 10% to 60%.

15. The preparing method according to claim 14, wherein the mass fraction of the inorganic particles is 25% to 50%.

16. The preparing method according to claim 10, wherein when a predetermined shear strain is applied to the artificial bone composite material, a storage modulus of the artificial bone composite material is equal to a loss modulus of the artificial bone composite material.

17. The preparing method according to claim 16, wherein:

when the shear strain applied to the artificial bone composite material is less than the predetermined shear strain, the storage modulus of the artificial bone composite material is greater than the loss modulus of the artificial bone composite material; and when the shear strain applied to the artificial bone composite material is greater than the predetermined shear strain, the loss modulus of the artificial bone composite material is greater than the storage modulus of the artificial bone composite material.

18. The preparing method according to claim 16, wherein the predetermined shear strain range is 20% to 80%.

\* \* \* \* \*